Feb. 23, 1960 G. J. VON ABRAMS Plant Pat. 1,915
ROSE PLANT
Filed Feb. 4, 1959
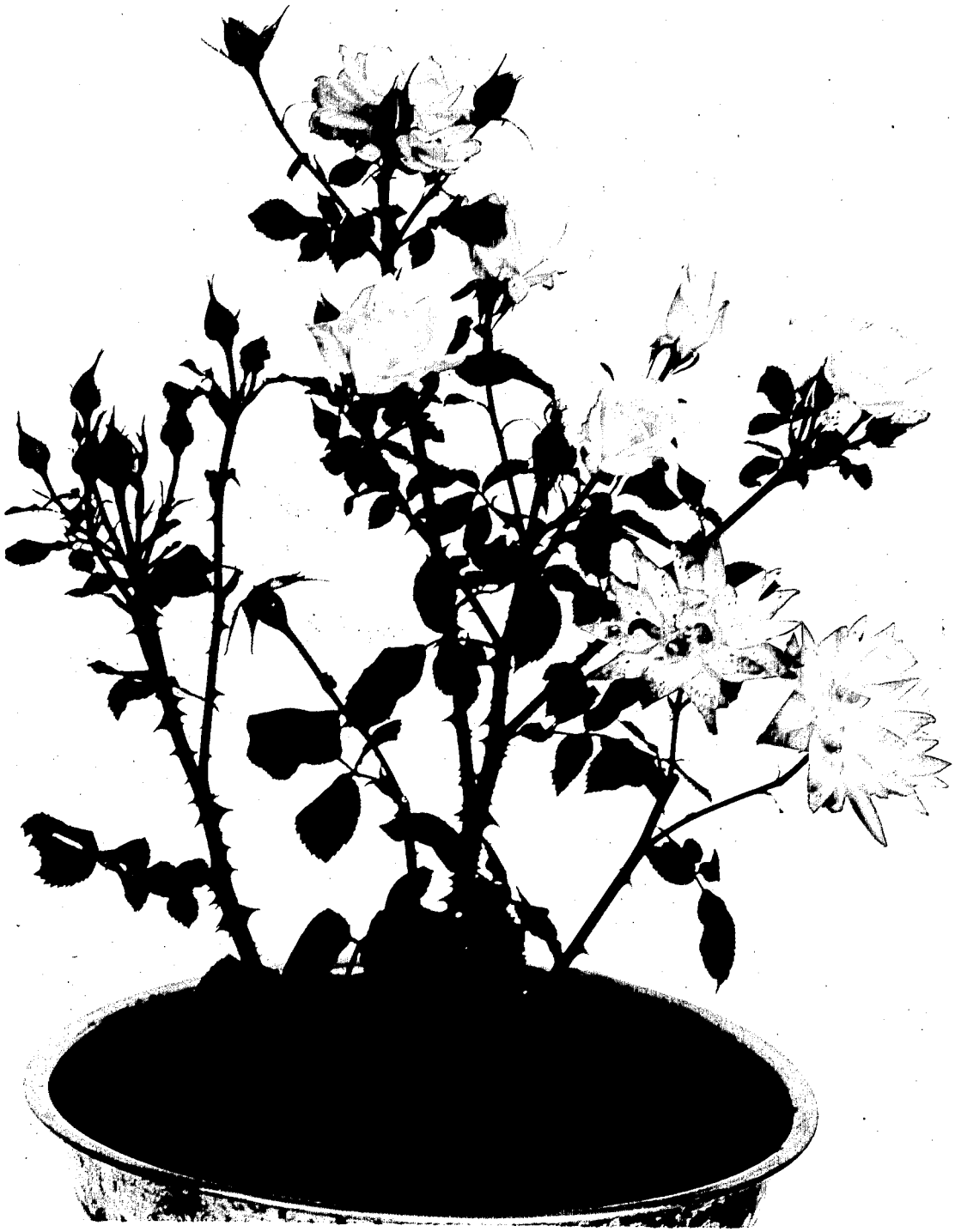
Inventor.
G. J. Von Abrams
By: Robb & Robb
Attorneys.

United States Patent Office

Plant Pat. 1,915
Patented Feb. 23, 1960

1,915

ROSE PLANT

Gordon J. von Abrams, Portland, Oreg., assignor to Eldon Pinkeney Dering, doing business as Peterson & Dering, Scappoose, Oreg.

Application February 4, 1959, Serial No. 791,242

1 Claim. (Cl. 47—61)

The present invention relates to a new and distinct variety of rose plant of the floribunda class, which was originated by me by crossing the variety "Pinocchio" (Plant Patent No. 484) with an unnamed and unpatented seedling derived from a cross of "Fashion" (Plant Patent No. 789) × "Orange Triumph" (unpatented).

The objective in part of this breeding was to produce a new rose variety having a lower growth and more compact plant habit than that of its seed parent "Pinocchio," combined with an improvement over the bud and flower form of the seed parent, with heavier petalage than that of the pollen parent, and having flowers of an attractive color falling within a desirable color range. These objectives were achieved, along with other improvements, as evidenced by the following phenotypic characteristics which are outstanding in the new variety and which distinguish it from its parents as well as from all other varieties of which I am aware:

(1) A compact, bushy and low-growing plant habit;
(2) Moderately glossy, medium-sized foliage;
(3) A free-flowering habit which is nearly continuous throughout the growing season, with the flowers borne in rounded clusters of medium size; and
(4) An unusual and distinctive combination of flower form and color.

In comparison with its seed parent, "Pinocchio," the plant of the new variety is smaller and more compact; the rachis is heavier, with more and larger thorns and more cilia; the flower is generally larger and higher-centered; and the flowers are more orange and less pink in color.

Asexual reproduction of my new variety by budding, as performed by me at Scappoose, Oregon, shows that the foregoing characteristics and distinctions come true to form and are established and transmitted through succeeding propagations.

The accompanying drawing shows typical specimens of the vegetative growth and flowers of my new variety in different stages of development, as they appeared in October, 1958 at Scappoose, Oregon, and as depicted in color as nearly true as it is reasonably possible to make the same in a color illustration of this character.

The following is a detailed description of my new variety, with color terminology in accordance with Robert F. Wilson's Horticultural Colour Chart (hereinafter abbreviated as 'Wilson"), Robert Ridgway's Color Standards and Nomenclature (hereinafter abbreviated as "Ridgway"), and the Nickerson Color Fan (hereinafter abbreviated as "Nickerson"), except where general color terms of ordinary dictionary significance are obvious:

Type: Hardy; compact; bush; seedling; for outdoor cut flowers and for garden decoration.
Class: Floribunda.
Breeding: Seedling.
*Seed parent.*—"Pinocchio."
*Pollen parent.*—An unnamed seedling of "Fashion" × "Orange Triumph."
Propagation: Holds its distinguishing characteristics through succeeding propagations by budding.

*Flower*

Locality where grown and observed: Scappoose, Oregon.
Flowers borne: Many per stem; in large, rounded clusters; on moderately strong, short pedicels.
Quantity of bloom: Abundant, outdoors.
Continuity: Nearly continuous during growing season.
Fragrance: Medium heavy; sweet.
Bud:
*Pedicel.*—Short (from 3 cm. to 5.5 cm.); medium caliper; erect; slightly rough; few reddish thorns; numerous glandular cilia. Color—near Strong Yellow Green, Plate 5 GY 6/8 (Nickerson).
*Before calyx breaks.*—Size—medium (20 mm. x 12 mm., excluding receptacle). Form—medium pointed; with a conspicuous neck; with a few foliaceous appendages on lateral margins of outer sepals; with slender, entire foliaceous parts extending beyond the tip of the bud ¼ or less than the length of the bud. Color—near Strong Yellow Green, Plate 7.5 GY 6/8 (Nickerson), often flushed red.
*As calyx breaks.*—Exposed petal color—near Brilliant Greenish Yellow, Plate 10 Y 9/9 (Nickerson), flushed near Strong Red, Plate 5 R 4/12 (Nickerson) where exposed to light.
*As first petal opens.*—Size—medium. Form—urn-shaped. Color: outside—Brilliant Yellow, Plate 2.5 Y 9/9 (Nickerson), flushed from pink to Cardinal Red, Plate 822/2, page 168 (Wilson); inside—French Rose, Plate 520/1, page 136 (Wilson), with base Sulphur Yellow, Plate 1, page 1 (Wilson).
*Opening.*—Opens up well except in extended periods of cold, wet weather.

Bloom:
*Size.*—Medium (about 7 cm. to 9 cm.).
*Petalage.*—Double; from 28 to 35 petals; arranged regularly.
*Form.*—High-centered to senescence; petals being slightly cupped inward at first, but gradually rolling outward at apex.

Petals:
*Texture.*—Medium thick; leathery. Inside—satiny. Outside—shiny.
*Shape.*—Outer petal—broadly obovate (about 4 cm. x 4 cm.), with shallow, irregular apical notch. Intermediate petal—obovate, with apical margin entire or irregular. Inner petal—obovate (about 2 cm. x 3 cm.), with apical margin irregular and sometimes mucronate; irregular petaloids sometimes occur.

Color: The color of this variety is extremely variable with environment, particularly with high light intensity and temperature, which cause exposed areas of the inside surface of the petals to become darker, less yellow and more red. The general color of the senescent bloom is frequently as dark as Geranium Lake, Plate 20/1, page 20 (Wilson). Beneath overlapping petals, where not exposed to light, this red pigment does not develop, and the pigments present degenerate rapidly with the onset of senescence, leaving these areas white or near white. At high temperature, the red pigment next breaks down between veins near the apex, leaving a white-mottled appearance.

This description of a newly-opened flower was made from a rose that was grown outdoors in the month of September, at Scappoose, Oregon:

*Color.*—Outer petal: outside surface—Geranium Lake, Plate 20/3, page 20 (Wilson), with small basal spot of Aureolin, Plate 3, page 3 (Wilson), fading upward to Aureolin, Plate 3/3, page 3 (Wilson); inside surface—Geranium Lake, Plate 20/3, page 20 (Wilson), deepening shortly upward to Geranium Lake, Plate 20/2, page 20 (Wilson); with basal spot of Aureolin, Plate 3, page 3 (Wilson) larger than that of the outside surface. Intermediate petal: outside surface—very small basal mark of Aureolin, Plate 3, page 3 (Wilson), fading sharply Aureolin, Plate 3/3, page 3 (Wilson). This flushes gradually upward to Vermilion, Plate 18/3, page 18 (Wilson); inside surface—larger basal mark of Aureolin, Plate 3, page 3 (Wilson), fading slightly upward to Aureolin, Plate 3/2, page 3 (Wilson), blending upward with the predominant color, between Vermilion, Plate 18/2, page 18 (Wilson) and Vermilion, Plate 18/3, page 18 (Wilson). Inner petal: outside surface—Aureolin, Plate 3/3, page 3 (Wilson), blending upward into a smaller apical area of Vermilion, Plate 18/3, page 18 (Wilson); color intensity slightly lower than in the case of intermediate petal, with very small basal mark of Aureolin, Plate 3, page 3 (Wilson); inside surface—between Fire Red, Plate 15/2, page 15 (Wilson) and Fire Red, Plate 15/3, page 15 (Wilson), with basal mark of Aureolin, Plate 3, page 3 (Wilson), fading slightly upward to Aureolin, Plate 3/2, page 3 (Wilson).

This description was made from a rose that was open for 3 days outdoors in the month of September, at Scappoose, Oregon:

*Color.*—Outer petal: outside surface—near white, flushed near apex between Geranium Lake, Plate 20/3, page 20 (Wilson) and Geranium Lake, Plate 20/2, page 20 (Wilson), with small basal mark of Aureolin, Plate 3, page 3 (Wilson); inside surface—near white, merging above with Geranium Lake, Plate 20/3, page 20 (Wilson), with sharply defined apical margin of Geranium Lake, Plate 20/1, page 20 (Wilson) where not shaded by inner petals; basal mark of Aureolin, Plate 3, page 3 (Wilson). Intermediate petal: outside surface—near white, flushed near apex between Geranium Lake, Plate 20/3, page 20 (Wilson) and Geranium Lake, Plate 20/2, page 20 (Wilson), with small basal mark of Aureolin, Plate 3, page 3 (Wilson); inside surface—near white, merging above with Vermilion, Plate 18/2, page 18 (Wilson), with sharply defined apical margin of Vermilion, Plate 18/3, page 18 (Wilson) where not shaded by inner petals; basal mark of Aureolin, Plate 3, page 3 (Wilson). Inner petal: outside surface—near white, flushed near apex between Geranium Lake, Plate 20/3, page 20 (Wilson) and Geranium Lake, Plate 20/2, page 20 (Wilson), with small basal mark of Aureolin, Plate 3, page 3 (Wilson); inside surface—exposed apical area between Vermilion, Plate 18/2, page 18 (Wilson) and Vermilion, Plate 18/3, page 18 (Wilson), with remainder near white, merging upward with Geranium Lake, Plate 20/3, page 20 (Wilson); basal mark of Aureolin, Plate 3, page 3 (Wilson).

*General color effect.*—Newly opened flower—Shrimp Pink, Plate I, 5.00–R.f (Ridgway). 3-days open—Eosine Pink, Plate I, 1.d (Ridgway) or darker.

*Behavior.*—Petals drop off cleanly; fade gradually lighter pink under most weather conditions, but under high temperature and light intensity, a red color develops in exposed areas, fading irregularly to near white, frequently creating a mottled appearance.

*Flower longevity.*—On bush in garden—5 days in September. Cut flowers grown outdoors and kept at living-room temperatures—3 days in September.

*Reproductive organs*

Stamens: Moderate number; arranged regularly about pistils between calyx and rim of receptacle.

Filaments: Medium length (about 2 mm. to 8 mm.); all with anthers. Color—near Brilliant Yellow, Plate 5 Y 9/9 (Nickerson).

Anthers: Small (about 1.5 mm. x 2 mm.); open over a short period of time. Color—near Moderate Orange Yellow, Plate 10 YR 8/10 (Nickerson).

Pollen: Moderately abundant. Color—varies from yellow to orange.

Pistils: Medium number.

Styles: Relatively even length (about 6 mm. to 9 mm.); medium caliper; loosely bunched.

Stigma: Small. Color—light greenish gray.

Ovaries: All enclosed in receptacle.

Hips: Small (about 11 mm. x 15 mm.); obovate; without conspicuous neck; walls relatively smooth, medium thin and fleshy. Color (mature)—near Strong Reddish Orange, Plate 10 R 5/11 (Nickerson); varies with environment.

Sepals: Persistent; medium size (about 0.9 cm. x 2.2 cm.); spear-shaped; folded straight down. Color—near Brilliant Yellow Green, Plate 7.5 GY 8/7 (Nickerson), but more gray; sometimes flushed with maroon.

Seeds: Medium number; medium small.

*Plant*

Foliage:

*Leaves.*—Compound of usually 5 leaflets; moderately abundant; hard; moderately heavy texture; medium glossy.

*Leaflets.*—Shape—from ovate to near oval, with apex mucronate. Base—rounded; sometimes slightly acute. Margin—simply serrate. Size—3 cm. x 5 cm.

*Color.*—Mature: upper surface—near Dusky Yellowish Green, Plate XLI, 29'''.GG–Y.m (Ridgway); under surface—near Deep Dull Yellow Green (1), Plate XXXII, 31''.Y–G.k (Ridgway). Young: upper surface—near Scheele's Green, Plate 860, page 175 (Wilson), with narrow maroon margin; under surface—near Chromium Green, Plate XXXII, 31''.Y–G.i (Ridgway), with variable maroon flush.

*Rachis (the supporting stem of the compound leaf).*—Medium heavy. Upper side—central groove smooth, with numerous glandular cilia on lateral ridges. Under side—several thorns; with few short glandular cilia.

*Stipules.*—Medium long and narrow (about 15 mm. x 5 mm.); with medium points turning out at an angle of about 45°; sometimes recurved.

*Disease resistance.*—Average resistance to mildew, rust and blackspot, as determined by field and garden observation and comparison with other varieties grown under comparable cultural conditions in various areas, including Scappoose, Oregon.

Growth:

*Habit.*—Small and compact bush (about 2 feet); much-branched.

*Growth.*—Moderately vigorous.

*Canes.*—Medium caliper.

*Main stems.*—Color—between Brilliant Yellowish Green, Plate 10 GY 7/8 (Nickerson) and Strong Yellow Green, Plate 7.5 GY 7/9 (Nickerson). Thorns—numerous; short; hooked slightly downward; with short oval base (about 3 mm. x 6.5 mm.). Prickles—from several to numerous; color—reddish brown. Hairs—none.

*Branches.* — Color — between Brilliant Yellowish Green, Plate 10 GY 7/8 (Nickerson) and Strong Yellow Green, Plate 7.5 GY 7/9 (Nickerson). Thorns—numerous; short; hooked slightly downward; with short oval base (about 3 mm. x 6.5 mm.). Prickles—from several to numerous, color—reddish brown. Hairs—none.

*New shoots.*—Color—near Strong Yellow Green, Plate 7.5 GY 7/9 (Nickerson), but more gray and heavily flushed with Dark Red, Plate 2.5 R 3/7 (Nickerson). Thorns—several; short (about 4 mm.); hooked moderately downward; with medium oval base, color—reddish. Prickles—several; some glandular. Hairs—none.

I claim:

A new and distinct variety of rose plant of the floribunda class, substantially as herein shown and described, characterized particularly as to novelty by the unique combination of a compact, bushy and low-growing plant habit, moderately glossy, medium sized foliage, a free-flowering habit which is nearly continuous throughout the growing season, with the flowers borne in rounded clusters of medium size, and an unusual and distinctive combination of flower form and color.

No references cited.